United States Patent [19]
Bentley et al.

[11] Patent Number: 5,990,237
[45] Date of Patent: Nov. 23, 1999

[54] POLY(ETHYLENE GLYCOL) ALDEHYDE HYDRATES AND RELATED POLYMERS AND APPLICATIONS IN MODIFYING AMINES

[75] Inventors: Michael D. Bentley; J. Milton Harris, both of Huntsville, Ala.

[73] Assignee: Shearwater Polymers, Inc., Huntsville, Ala.

[21] Appl. No.: 09/082,063

[22] Filed: May 20, 1998

[51] Int. Cl.[6] .......................... C07C 103/52; C08L 89/00
[52] U.S. Cl. ........................ 525/54.2; 525/56; 525/107; 525/154
[58] Field of Search ........................... 525/54.2, 56, 107, 525/154

[56] References Cited

U.S. PATENT DOCUMENTS

| | | |
|---|---|---|
| 4,179,337 | 12/1979 | Davis et al. . |
| 4,487,715 | 12/1984 | Nitecki et al. .................. 260/112.5 R |
| 5,171,264 | 12/1992 | Merrill . |
| 5,252,714 | 10/1993 | Harris et al. . |

OTHER PUBLICATIONS

Functionalized Poly(ethylene glycol) for Preparation of Biologically Conjugates, *Bioconjugate Chem.* 1995, 6: 150–165, Samuel Zalipsky.

Modification of CD4 Immunoadhesin with Monomethoxpoly(ethylene glycol) Aldehyde via Reductive Alkylation, *Bioconjugate Chem.* 1994, 5: 133–140, Steven M. Chamow, et al.

*Primary Examiner*—Nathan M. Nutter
*Attorney, Agent, or Firm*—Alston & Bird LLP

[57] ABSTRACT

The present invention provides a method of coupling PEG or related polymers to a substance by reductive amination. An activated PEG having an aldehyde hydrate moiety is prepared and is conveniently used as an intermediate for coupling PEG to a variety of biomolecules by reductive amination. The method of making PEG-conjugated biomolecules in accordance with the present invention avoids the condensation and oxidation reactions that are inherent in the coupling methods employed heretofore in the prior art using PEG aldehyde. As a result, high purity of PEG-conjugates can be achieved.

23 Claims, No Drawings

POLY(ETHYLENE GLYCOL) ALDEHYDE HYDRATES AND RELATED POLYMERS AND APPLICATIONS IN MODIFYING AMINES

FIELD OF THE INVENTION

This invention generally relates to methods of modifying a substance with a hydrophilic polymer, and particular to methods of coupling a poly(ethylene glycol) polymer to a biomaterial.

BACKGROUND OF THE INVENTION

Covalent attachment of the hydrophilic polymer poly (ethylene glycol) ("PEG"), also known as poly(ethylene oxide) ("PEO"), to molecules and surfaces has important applications, including in biotechnology and medicine. In its most common form, PEG is a linear polymer having hydroxyl groups at each terminus:

This formula can be represented in brief as HO—PEG—OH where it is understood that —PEG— represents the following structural unit:

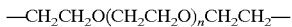

n typically ranges from approximately 10 to 2000.

PEG is commonly used as methoxy-poly(ethylene glycol), or mPEG in brief, in which one terminus is the relatively inert methoxy group, while the other terminus is a hydroxyl group subject to ready chemical modification:

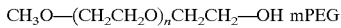

Similarly, other alkoxy groups such as benzyloxy and tert-butoxy can be substituted for methoxy in the above formula.

Branched PEGs are also commonly used. The branched forms can be prepared by addition of ethylene oxide to various polyols, including glycerol, pentaerythritol and sorbitol. For example, the four-armed branched PEG prepared from pentaerythritol is shown below:

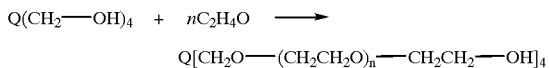

Branched PEGs can be represented as Q(—PEG—OH)$_n$ in which Q represents a central core molecule such as pentaerythritol or glycerol, and n represents the number of arms which can range from three to a hundred or more. The hydroxyl groups are readily subject to chemical modification.

The copolymers of ethylene oxide and propylene oxide are closely related to PEG in their chemistry, and they can be substituted for PEG in many of its applications.

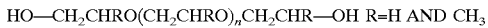

PEG is a useful polymer having the property of water solubility as well as solubility in many organic solvents. PEG is also non-toxic and non-immunogenic. When PEG is chemically attached to a water insoluble compound, the resulting conjugate generally is water soluble as well as soluble in many organic solvents. When the molecule to which PEG is attached is biologically active, such as a drug, this activity is commonly retained after attachment of PEG and the conjugate may display altered pharmacokinetics. For example, it has been demonstrated that the water insoluble antimalarial, artemisinin, becomes water soluble and exhibits increased antimalarial activity when coupled to PEG. See Bentley et al., *Polymer Preprints,* 38(1):584 (1997).

U.S. Pat. No. 4,179,337 to Davis et al. discloses that proteins coupled to PEG have enhanced blood circulation lifetime because of reduced kidney clearance and reduced immunogenicity. The lack of toxicity of the polymer and its rapid clearance from the body are advantageous for pharmaceutical applications.

To couple PEG to a molecule such as a protein or a small drug molecule, it is necessary to use an "activated derivative" of the PEG having a functional group at the terminus suitable for reaction with a group on the other molecule. For example, the hydroxyl group of CH$_3$O—PEG—OH can be converted to an aldehyde group, and this aldehyde group can then be covalently linked to a molecule or surface bearing one or more amine groups using the method of reductive amination. An example of this approach is described in U.S. Pat. No. 5,252,714 to Harris and Herati. The patent describes the preparation of PEG propionaldehyde,

and its reaction in reductive amination of amine-bearing surfaces and molecules. Similarly, methoxy-PEG acetaldehyde,

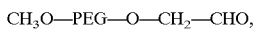

was also used to link methoxy-PEG to a protein by reductive amination. See Chamow et. al. *Bioconjugate Chemistry,* 5:133(1994). In reductive amination the aldehyde and amine are mixed with a reducing agent, such as NaCNBH$_3$, to provide a new amine:

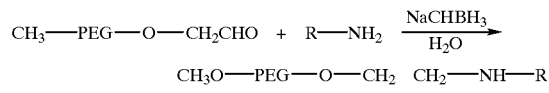

However, as Zalipsky pointed out in reviewing activated PEGs for preparation of conjugates, the use of PEG acetaldehyde has been limited by its high reactivity, which leads to condensation side reactions. See *Bioconjugate Chemistry,* 6:150 (1995). In addition, PEG acetaldehyde has also proven difficult to prepare in high purity. For example, in the above-discussed reductive amination in which methoxy-PEG acetaldehyde, CH$_3$O—PEG—O—CH$_2$—CHO, was used to link methoxy-PEG to a protein, the purity of the methoxy-PEG acetaldehyde was only 52%. The impurity causes serious difficulties in forming PEG-biomolecule conjugates because of the required subsequent purification steps and loss of valuable bioactive molecules, such as proteins.

Oxidation reactions are problematic when working with aldehydes. Aldehydes in general are known to be subject to facile oxidation to form carboxylic acids. This oxidation can occur during isolation, purification, use or storage. These oxidized aldehydes typically are not desirable for conjugation with biomolecules. Oxidation results in a number of impurities and the reaction products are difficult to isolate.

Thus, the PEG aldehydes known heretofore in the art proved to be unsatisfactory for coupling PEG or its derivatives to biomolecules. The condensation and oxidation reactions substantially limit the uses of these PEG aldehydes. Therefore, there is need for improved methods of coupling PEG to biomolecules.

SUMMARY OF THE INVENTION

This invention provides a method for conjugating PEG and related polymers with substances including biomaterials and biologically active materials. This method includes in situ preparation of PEG aldehyde hydrates, which can then be used in solution, without isolation, to form conjugates by reductive amination with a range of biologically active molecules, including proteins, peptides, polysaccharides, oligonucleotides, and small drug molecules. The great advantage of PEG aldehyde hydrates and the in situ method of the invention is that the hydrates do not have to be isolated by removing them from water. Therefore, this method avoids the condensation and oxidation reactions that previously have been drawbacks. Conjugates of high purity can be achieved using this method.

Specifically, the method of this invention comprises preparing in situ an activated PEG having an aldehyde hydrate moiety and reacting the activated PEG directly with a substance containing an amine group without having isolated the activated PEG. An activated PEG having an aldehyde hydrate moiety can be prepared in situ by first linking a PEG polymer with a functional group that can be converted to an aldehyde hydrate moiety, and then hydrolyzing the resulting polymer at an acidic pH. The suitable functional group may have a formula of

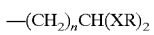

OR

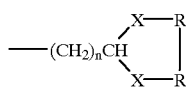

wherein n is a number of from 1 to 6, X is oxygen O or sulfur S, and R is an alkyl group. The two R groups can be linked or not linked. The linkage between the moiety and the polymer is hydrolytically stable. Typically, the functional group is an acetalaldehyde diethyl acetal moiety or propionaldehyde diethyl acetal moiety, in which n is 1 or 2, respectively.

A substance to be conjugated is added to the reaction mixture, containing the activated polymer having an aldehyde hydrate moiety. The activated PEG polymer in the reaction mixture can readily react with the added substance by reductive amination between the aldehyde hydrate moiety and an amine group in the substance in the presence of a reducing agent.

In place of the linear PEG polymers, a variety of other polymer forms can be conjugated to an amine-containing substance using the method of this invention. Examples of suitable polymer forms include but are not limited to linear or branched or dendritic or star structures, degradable structures, hydrogel forming structures, and others. Other suitable polymers include poly(vinyl alcohol) ("PVA"); other poly(alkylene oxides) such as poly(propylene glycol) ("PPG") and the like; and poly(oxyethylated polyols) such as poly(oxyethylated glycerol), poly(oxyethylated sorbitol), and poly(oxyethylated glucose); poly(olefinic alcohols); poly(acryloyl morpholine); poly(vinyl pyrrolidone); poly (oxazoline); poly(hydoxyethyl methacrylate), and dextran, and the like.

Amine-containing substances suitable for modification using the method of this invention may include a variety of biomaterials such as peptides, proteins, polysaccharides, oligonucleotides, and the like. Particularly, many drug molecules or carriers are suitable for conjugation.

Thus, this invention provides a method of conjugating a hydrophilic polymer to a substance by reductive amination. An activated polymer having an aldehyde hydrate moiety is used as an intermediate for coupling the polymer to a variety of biomolecules by reductive amination. The methods of making PEG-conjugated biomolecules in accordance with the present invention avoid the condensation and oxidation reactions that are inherent in the coupling methods employed heretofore in the prior art using PEG aldehyde. As a result, high purity of PEG-conjugates can be achieved.

DETAILED DESCRIPTION

The present invention provides a method of conjugating a hydrophilic polymer to a biological material by reductive amination. The conventional technique for this purpose includes first purifying an activated polymer having an aldehyde moiety. The method of the present invention obviates the need for conventional purification of the activated polymer and avoids the condensation and oxidation reactions inherent in the conventional methods. The method of this invention employs a polymer having an active moiety of aldehyde hydrate which is formed in solution and is capable of reacting with a substance by reductive amination.

A poly(ethylene glycol) PEG molecule or a PEG derivative is used as the hydrophilic polymer for conjugation. The starting PEG polymer molecule has at least one hydroxyl moiety, —OH, that is available to participate in chemical reactions and is considered to be an "active" hydroxyl moiety. The PEG molecule can have multiple active hydroxyl moieties available for chemical reaction, as is explained below. These active hydroxyl moieties are in fact usually nonreactive with biological materials, and the first step in the synthesis is to prepare a PEG having a more reactive moiety.

The terms "group," "functional group," "moiety," "active moiety," "reactive site," and "radical" are somewhat synonymous in the chemical arts and are used in the art and herein to refer to distinct, definable portions or units of a molecule and to units that perform some function or activity and are reactive with other molecules or portions of molecules. In this sense a protein or a protein residue can be considered a molecule or as a functional group or moiety when coupled to a polymer.

The term "PEG" is used in the art and herein to describe any of several condensation polymers of ethylene glycol having the general formula represented by the structure $H(OCH_2CH_2)_nOH$. PEG is also known as polyoxyethylene, polyethylene oxide, polyglycol, and polyether glycol. PEG can be prepared as copolymers of ethylene oxide and many other monomers.

Poly(ethylene glycol) is used in biological applications because it has properties that are highly desirable and is generally approved for biological or biotechnical applications. PEG typically is clear, colorless, odorless, soluble in water, stable to heat, inert to many chemical agents, does not hydrolyze or deteriorate, and is nontoxic. Poly(ethylene glycol) is considered to be biocompatible, which is to say that PEG is capable of coexistence with living tissues or organisms without causing harm. More specifically, PEG is not immunogenic, which is to say that PEG does not tend to produce an immune response in the body. When attached to a moiety having some desirable function in the body, the PEG tends to mask the moiety and can reduce or eliminate any immune response so that an organism can tolerate the presence of the moiety. Accordingly, the PEG polymers of the invention should be substantially non-toxic and should not tend substantially to produce an immune response or cause clotting or other undesirable effects.

The first step of the method of conjugating is to link to the PEG polymer a moiety that can be conveniently converted or hydrolyzed to an aldehyde hydrate group. This moiety should not be an aldehyde group. In a preferred embodiment of the present invention, the moiety to be linked to the PEG polymer has a formula of —(CH$_2$)$_n$CH(XR)$_2$

OR

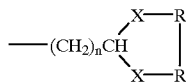

wherein n is a number of from 1 to 6, X is the atom of O or S, and R is an alkyl group. The two R groups can be linked together or not linked. The linkage between the moiety and the polymer is hydrolytically stable.

As indicated by the formula, the moiety to be linked to PEG polymer can be a variety of groups, e.g., diethyl acetal group (when n=1, X is oxygen atom, R is an alkyl group with two carbons), propionaldehyde diethyl acetal group (n=2, X is oxygen atom, R is an alkyl group with two carbons). Preferably, the moiety is diethyl acetal group.

The linking can be done by reacting a PEG polymer having at least one hydroxyl group with a halide substituted compound having a formula of Halide-(CH$_2$)$_n$CH(XR)$_2$

OR

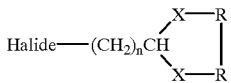

wherein n is a number of from 1 to 6, X is the atom of O or S, and R is an alkyl group. The two R groups can be linked or not linked to each other. The reaction is completed in the presence of for example, sodium hydroxide.

The second step is to convert the above polymer precursor to an activated organic polymer having an active aldehyde hydrate moiety. This hydrolysis is done conveniently in situ in an aqueous solution at an acidic pH. Without being bound by any theory, it is believed that the conversion is a result of the reaction of the moiety in the precursor polymer with water. An acidic pH in the reaction mixture can be generated by adding acids to the reaction which is generally known in the art. For example, acetic acid, phosphoric acid, trifluoroacetic acid are all suitable. The reaction time required for the conversion can vary with temperature and the acid used. Typically, the time required for complete hydrolysis is shorter when a higher temperature is maintained. In addition, lower pH leads to shorter duration required for complete hydrolysis.

A substantially complete conversion from the polymer precursor to the aldehyde hydrate polymer can be achieved in accordance with this invention. Spectroscopic tests can be performed to analyze the components in the reaction mixture after the conversion is completed. Substantially 100% conversion can be achieved with no detectable aldehyde derivative of the polymer present, particularly for the acetaldehyde.

The resulting activated organic polymer having an active aldehyde hydrate moiety can be readily used to react with a substance by reductive amination. In the reaction, the aldehyde hydrate moiety acts as a functional group and reacts with the amine group in the substance. In accordance with the present invention, in the conjugation step, the substance to which the PEG polymer to be conjugated is added to the reaction mixture directly. In addition, a reductive agent must be added to the reaction. An exemplary example of such a reductive agent is sodium cyanoborohydride(NaCNBH$_3$). Specifically, the conjugation is by reductive amination. Thus, the substance must contain an amine group on its surface or particle. The substance can be selected from, e.g., proteins, peptides, oligonucleotides, polysaccharides and small drug molecules. Broadly speaking, any material having a reactive amine group accessible to the activated polymer having an aldehyde hydrate group can be used in the present invention.

A conjugation reaction of this type can be represented as follows:

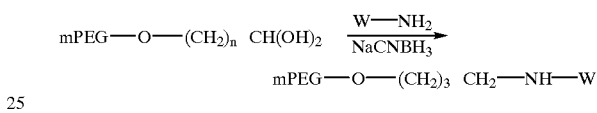

As used herein, mPEG represents a methoxy-poly(ethylene glycol). W—NH$_2$ represents a substance having an amine group.

The activated organic polymer having an active aldehyde hydrate moiety can be of any molecular weight and can be linear or branched with hundreds of arms. The PEG can be substituted or unsubstituted so long as at least one reactive site is available for conversion into an aldehyde hydrate moiety. PEG typically has average molecular weights of from 200 to 100,000 and its biological properties can vary with molecular weight and depending on the degree of branching and substitution, so not all of these derivatives may be useful for biological or biotechnical applications. For many biological and biotechnical applications, substantially linear, straight-chain PEG acetaldehyde hydrate is useful, substantially unsubstituted except for the acetaldehyde hydrate moieties and, where desired, other additional functional groups. The PEG can be capped on one end with a relatively nonreactive moiety such as a moiety selected from the group consisting of alkyl moieties, typically methyl, benzyl moieties and aryl moieties. The capped form can be useful, for example, if it is desirable simply to attach the polymer chains at various amine sites along a protein chain. Attachment of PEG molecules to a biologically active molecule such as a protein or other pharmaceutical or to a surface is sometimes referred to as "PEGylation."

A linear PEG with active hydroxyls at each end can be activated at each end to have an aldehyde hydrate group at each end. This type of activated PEG is said to be homobifunctional. The bifunctional structure, PEG bis aldehyde hydrate, for example, a dumbbell structure and can be used, for example, as a linker or spacer to attach a biologically active molecule to a surface or to attach more than one such biologically active molecule to the PEG molecule. In addition, bifunctional activated PEG can be used to crosslink biological materials such proteins, aminopolysacchrides such as chitosan to form hydrogel.

Another form of activated PEG aldehyde hydrate is dendritic activated PEG in which multiple arms of PEG are attached to a central core structure. Dendritic PEG structures can be highly branched and are commonly known as "star"

molecules. Examples of suitable molecules for the core include but not limited to glycerol, lysine, pentaerythritol. A "star" molecule can be represented by the formula of Q[poly]$_y$.

Wherein Q is a branching core moiety and y is from 2 to about 100. Star molecules are generally described in U.S. Pat. No. 5,171,264 to Merrill, the contents of which are incorporated herein by reference. The aldehyde hydrate moiety can be used to provide an active, functional group on the end of the PEG chain extending from the core and as a linker for joining a functional group to the star molecule arms. Additionally, the aldehyde hydrate moiety can also be linked directly to the core molecule having PEG chains extending from the core. One example of such a dendritic activated PEG has a formula of

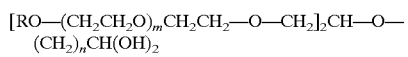

[RO—(CH$_2$CH$_2$O)$_m$CH$_2$CH$_2$—O—CH$_2$]$_2$CH—O—(CH$_2$)$_n$CH(OH)$_2$ wherein R is H, alkyl, benzyl, or aryl; m ranges from about 5 to about 3000, n ranges from 1 to 6.

Another example of such a dendritic activated PEG is the polymer which is represented by the formula of

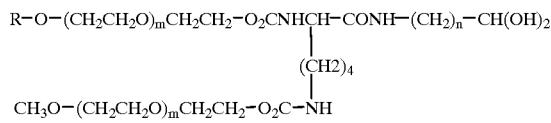

in which m ranges from about 5 to 3000, and n is about 1 to 6. In the formula, R represents a hydrogen atom, or an alkyl, benzyl or aryl group.

A branched form of PEG and related polymers is also described in recent patent application U.S. Ser. No. 08/443,383, filed May 17th, 1995 under the title Multi-armed, Monofunctional, and Hydrolytically Stable Derivatives of Poly(ethylene glycol) and Related Polymers for Modification of Surfaces and Molecules. The branched form has a single terminus that is subject to ready chemical modification. This type of PEG can be represented as (CH$_3$O—PEG—)$_p$R—X, where p equals 2 or 3, R represents a central core such as lysine or glycerol, and X represents a group such as carboxyl that is subject to ready chemical activation.

PEG aldehyde hydrate and its derivatives can be used for attachment directly to surfaces and molecules having an amine moiety. However, a heterobifunctional PEG derivative having a aldehyde hydrate moiety on one terminus and a different functional moiety on the opposite terminus group can be attached by the different moiety to a surface or molecule. When substituted with one of the other active moieties, the heterobifunctional PEG dumbbell structure can be used, for example, to carry a protein or other biologically active molecule by amine linkages on one end and by another linkage on the other end, such as sulfone linkage, to produce a molecule having two different activities. A heterobifunctional PEG having an amine specific moiety on one end and a sulfone moiety on the other end could be attached to both cysteine and lysine fractions of proteins. A stable sulfone linkage can be achieved and then the hydrolytically stable unreacted aldehyde hydrate moiety is available for subsequent amine-specific reactions as desired.

Other active groups for heterobifunctional aldehyde hydrate-activated PEGs can be selected from among a wide variety of compounds. For biological and biotechnical applications, the substituents would typically be selected from reactive moieties typically used in PEG chemistry to activate PEG such as the trifluoroethylsulfonate, which is also sometimes called tresylate, n-hydroxylsuccinimide ester, cyanuric chloride, cyanuric fluoride, acyl azide, succinate, the p-diazo benzyl group, the 3-(p-diazophenyloxy)-2-hydroxy propyloxy group, and others. Examples of active moieties are shown in Davis et al. U.S. Pat. No. 4,179,337; Lee et al. U.S. Pat. Nos. 4,296,097 and 4,430,260; Iwasaki et al. U.S. Pat. No. 4,670,417; Katre et al. U.S. Pat. Nos. 4,766,106; 4,917,888; and 4,931,544; Nakagawa et al. U.S. Pat. No. 4,791,192; Nitecki et al. U.S. Pat. Nos. 4,902,502 and 5,089,261; Saifer U.S. Pat. No. 5,080,891; Zalipsky U.S. Pat. No. 5,122,614; Shadle et al. U.S. Pat. No. 5,153,265; Rhee et al. U.S. Pat. No. 5,162,430; European Patent Application Publication No. 0 247 860; and PCT International Application Nos. US86/01252; GB89/01261; GB89/01262; GB89/01263; US90/03252; US90/06843; US91/06103; US92/00432; and US92/02047, the contents of which are incorporated herein by reference.

It should be apparent to the skilled artisan that the dumbbell structures discussed above could be used to carry a wide variety of substituents and combinations of substituents. Pharmaceuticals such as aspirin, vitamins, penicillin, and others too numerous to mention; polypeptides or proteins and protein fragments of various functionalities and molecular weights; cells of various types; surfaces for biomaterials, almost any substance could be modified. As used herein, the term "protein" should be understood to include peptides and polypeptides, which are polymers of amino acids. The term "biomaterial" means a material, typically synthetic and sometimes made of plastic, that is suitable for implanting in a living body to repair damaged or diseased parts. An example of a biomaterial is artificial blood vessels.

One straight chain activated PEG derivative for biological and biotechnical applications has the basic structure of

Z—O—(CH$_2$CH$_2$O(CH$_2$CH$_2$O)$_m$(CH$_2$)$_n$CH(OH)$_2$

The PEG monomer —OCH$_2$CH$_2$— preferably is substantially unsubstituted and unbranched along the polymer backbone. The letter "m" can equal from about 5 to 3,000. A more typical range is from about 5 to 2,200, which corresponds to a molecular weight of from about 220 to 100,000. Still more typical is a range of from about 34 to 1,100, which corresponds to a molecular weight range of from about 1,500 to 50,000. Most applications will be accomplished with molecular weights in the neighborhood of 2,000 to 5,000, which corresponds to a value of m of from about 45 to 110.

n ranges from 1 to 6. Z is selected from the group consisting of hydrogen, alkyl groups, benzyl groups and aryl groups.

The active polymer derivatives are water soluble and produce water soluble stable linkages with amine groups. The derivatives are considered infinitely soluble in water or as approaching infinite solubility and can enable otherwise insoluble molecules to pass into solution when conjugated with the derivative.

Other water soluble polymers than PEG are believed to be suitable for similar modification and activation with an active aldehyde hydrate moiety. These other polymers include poly(vinyl alcohol) ("PVA"); other poly(alkylene oxides) such as poly(propylene glycol) ("PPG") and the like; and poly(oxyethylated polyols) such as poly(oxyethylated glycerol), poly(oxyethylated sorbitol), and poly(oxyethylated glucose); poly(olefinic alcohols); poly(acryloyl morpholine); poly(vinyl pyrrolidone); poly(oxazoline); poly(hydoxyethyl methacrylate, and dextran, and the like. The polymers can be homopolymers or random or block copolymers and terpolymers based on the monomers of the above polymers, straight chain or branched, or substituted or unsubstituted similar to PEG, but having at least one active site available for reaction to form the aldehyde hydrate moiety.

In addition to the various linear and branched forms of PEG, the polymer can also be prepared with weak or degradable linkages in the backbone. It should be understood that the invention is applicable to these structures. U.S. Provisional Patent Application 60/026,716, filed Sep. 26, 1996 and entitled Soluble, Degradable, Poly(ethylene glycol) Derivatives for Slow Release of Bound Molecules into Solution shows that PEG can be prepared with ester linkages in the polymer backbone that are subject to hydrolysis. This hydrolysis results in cleavage of the polymer into fragments with lower molecular weight.

For example, suitable activated polymer also include a hydrolytically degradable form of PEG such as the polymer having the formula of R—O—CH$_2$CH$_2$O(CH$_2$CH$_2$O)$_m$(CH$_2$)$_r$—CO$_2$—(CH$_2$CH$_2$O)$_s$—(CH$_2$)$_n$CH(OH)$_2$.

In the formula, m and s may be the same or different and range from about 5 to about 3000. Similarly, n and r may be same or different and range from 1 to 6. R represents a hydrogen atom, or an alkyl, benzyl or aryl group.

In the present invention, a polymer having an aldehyde moiety can also be isolated with substantial purity. Once the activated polymer having an aldehyde hydrate moiety is made in situ at acidic pH, an organic solvent such as methylene chloride is added to and mixed with the reaction mixture. The aldehyde hydrate moiety linked to the polymer is converted to an aldehyde moiety in the organic phase and is extracted into the organic solvent. Drying and removal of the solvent is done by distillation in an inert atmosphere. Preferably, the compound is stored in the cold under an inert atmosphere. The aldehyde derivative of the polymer is substantially pure.

EXAMPLE 1

Preparation of mPEG$_{2000}$CH$_2$CH(OEt)$_2$

In one useful application of this method, mPEG$_{2000}$OH (MW=2000, 10 g, 0.005 moles, was dissolved in dioxane (250 ml) and 75 ml of solvent was distilled to azeotropically remove water. The solution was then cooled to room temperature and 3.8 ml (0.025 moles) of chloroacetaldehyde diethyl acetal was added under N$_2$. Powdered NaOH (2.0 g, 0.05 moles) was then added and the resulting suspension was stirred vigorously under reflux for 24 hours. An additional 80 ml of solvent was removed by distillation and refluxing was continued for 24 hours. After cooling to room temperature, the suspension was filtered and the filtrate evaporated to dryness under vacuum using a 50!C. bath. The residue was dissolved in 100 ml of water and the pH adjusted to 7.0 with dilute HCl. The solution was then extracted with three 75 ml portions of CH$_2$Cl$_2$ and the combined extracts dried over Na$_2$SO$_4$ and evaporated under vacuum to about 10 ml. Cold ethyl ether (250 ml) was added and the resulting precipitate was collected by vacuum filtration and dried under vacuum to obtain the product as a white powder (7.1 g). $^1$H nmr (200 Mhz, dmso-d-6) was useful in structural and purity determination. Particularly relevant was the PEG backbone absorption at 3.51 ppm, the ethyl triplet absorption at 1.11 ppm [(—CH$_2$CH$_3$], and the acetal triplet at 4.55 ppm [(—CH$_2$CH(OC$_2$H$_5$)$_2$]. Integration of the acetal triplet relative to the PEG backbone peak allowed determination of the degree of PEGylation to be 85–98% for mPEG acetals prepared by this method.

EXAMPLE 2 mPEG$_{2000}$ acetaldehyde hydrate

The mPEG acetaldehyde hydrate was generated in solution by heating a stirred solution of PEG$_{2000}$ acetaldehyde diethyl acetal under N$_2$ in aqueous H$_3$PO$_4$(pH 2) at 50!C. for 2 hours. NMR studies of this reaction in D$_3$PO$_4$/D$_2$O demonstrated the presence of PEG acetaldehyde hydrate in solution (4.97 ppm, triplet, —CH$_2$CH(OD)$_2$] as a product of these reactions. The following conditions result in 100% hydrolysis of mPEG$_{2000}$ acetaldehyde diethyl acetal:

| Solvent | pH | Temperature (?C) | Time |
|---|---|---|---|
| acetic acid/water | 2.6 | 37 | 44 h |
| acetic acid/water | 2.6 | 77 | 25 min |
| phosphoric acid/water | 2.0 | 37 | 8 h |
| phosphoric acid water | 2.0 | 50 | 2 h |
| phosphoric acid/water | 1.0 | 37 | 20 min |
| trifluoroacetic acid/water | 1.0 | 37 | 20 min |

EXAMPLE 3

Isolation of mPEG$_{2000}$ acetaldehyde

In a typical example, 1 g of mPEG$_{2000}$ acetaldehyde diethyl acetal was heated at 40–50!C. in 10 ml of aqueous phosphoric acid (pH 1) for 20 minutes or at pH 2 at 50!C. for 2 hours. After cooling the resulting solution to room temperature, the pH was carefully adjusted to 6 by dropwise addition of 5% aqueous sodium bicarbonate to the rapidly stirred solution. The resulting solution was saturated with NaCl and extracted with methylene chloride (3×20 ml). The extract was dried over Na$_2$SO$_4$, filtered, and the filtrate evaporated to about 10 ml under vacuum. Addition of cold ethyl ether (200 ml) precipitated the mPEG$_{2000}$ acetaldehyde which was collected by vacuum filtration and dried under vacuum at room temperature. The yield was 760 mg (76%) and the degree of substitution was 93% by $^1$H nmr. Gel permeation chromatography (Waters Ultrhydrogel 250, 7.8× 300 mm, phosphate buffer, pH 7.2) showed no higher molecular weight materials which would be formed by aldol condensation. The $^1$H nmr in d-6 DMSO displayed the characteristic PEG backbone absorption at 3.51 ppm and the aldehyde singlet at 9.57 ppm. When the nmr was recorded in D$_2$O, the triplet charactristic of the PEG aldehyde hydrate at 4.97 ppm was observed. The PEG acetaldehyde must be stored at low temperature under inert gas to prevent oxidation.

EXAMPLE 4

Preparation of BzO—PEG$_{3400}$—O—CH$_2$CH(OC$_2$H$_5$)$_2$

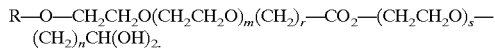

In a 3-necked, 500 ml round-bottom flask were placed 300 ml of dioxane and 14 g of BzO—PEG$_{3400}$—OH (MW= 3400, 0.0040 moles). The resulting solution was then azeotropically dried by distillation under N$_2$ of 130 ml of solvent. After cooling the solution, finely powdered NaOH (0.8 g, 0.02 moles) and ClCH$_2$CH(OC$_2$H$_5$)$_2$ (3 ml, 0.02 moles) were added under N$_2$ and the resulting suspension was rapidly stirred while refluxing over a 24 h period. Thirty ml of dioxane was then removed by distillation and the rapidly stirred solution was refluxed under $N_2$ for an additional 24 h. The suspension was then cooled and filtered with the addition of Celite™. The filtrate was evaporated under vacuum and 200 ml of ethyl ether was added to the residual oil. The resulting precipitate was collected by filtration and dried under vacuum at room temperature to obtain a tan powder (13.6 g). The powder was dissolved in $CH_2Cl_2$ (35 ml) and reprecipitated by the addition of 500 ml of cold ethyl ether. The precipitate was collected by filtration and dried under vacuum at room temperature to obtain 13.0 g of $BzO—PEG_{3400}—OCH_2CH(OC_2H_5)_2$ as a white powder (purity 94–98% by $^1H$ nmr). $^1H$ nmr (DMSO-$d_6$): d 1.11 (t, OC$\underline{H}_2$CH$_3$); 3.51 (br m, O—CH$_2$CH$_2$—O), 4.48 (s, C$_6$H$_5$—CH$_2$O); 4.55 (t,—C$\underline{H}$(OC$_2$H$_5$)$_2$), 7.32 (s, C$_6$H$_5$—)

EXAMPLE 5

Preparation of $HO—PEG_{3400}—OCH_2CH(OC_2H_5)_2$ $BzO—PEG_{3400}—OCH_2CH(OC_2H_5)_2$ (13 g) was dissolved in 150 ml of 95% ethanol and 6.5 g of 10% Pd on charcoal was added under $N_2$. The suspension was shaken 70 h under $H_2$ (40 psi) and the suspension filtered. The residual catalyst was washed with 2×25 ml of boiling chloroform and the washings combined with the ethanol filtrate and evaporated under vacuum to obtain a clear, colorless oil. To the oil was added 400 ml of cold ethyl ether and the resulting precipitate collected by filtration to obtain, after vacuum drying at room temperature, 11.3 g of $HO—PEG_{3400}—OCH_2CH(OC_2H_5)_2$ as a white powder (92% pure by $^1H$ nmr). $^1H$ nmr (DMSO-$d_6$): d 1.10, (t, OCH$_2$CH$_3$), 3.51(br m, OCH$_2$CH$_2$—O), 4.55, (m, HO+—CH(OCH$_2$CH$_3$)$_2$).

EXAMPLE 6

Pegylation of chitosan using $mPEG_{2000}$ acetaldehyde diethyl acetal

As a typical example, a solution of 720 mg of $mPEG_{2000}$ acetaldehyde diethyl acetal in 50 ml of aqueous acetic acid (pH 2.6) was heated at 65!C. for 1 hour. Chitosan (MW ca 200 KDa,; 50 mg) was added and the resulting solution cooled to room temperature. The pH was carefully adjusted to 5 with 5% aqueous $NaHCO_3$, 40 mg of $Na(CN)BH_3$ was added, and the resulting solution stirred 21 h at room temperature. The solution was then subjected to ultrafiltration (MWCO 30 KD) until a test with an acidified solution of polyacrylic acid showed no PEG in the filtrate. Freeze-drying of the residual solution yielded the PEGylated chitosan as a papery, white solid (315 mg) with 84 wt. % (48.7 mole %) PEGylation. GPC indicated less than 1% of unbound PEG in the product. Capillary electrophoresis indicated no chitosan was present and a new product was present having a migration time of 4.16 relative to that of chitosan. $^1H$ nmr in $D_2O$ showed absorptions characteristic of PEG and chitosan (3.51 ppm, br m, PEG backbone; 3.20 ppm, s, PEG CH$_3$O; 1.87 ppm, br s, chitosan Ac CH$_3$; 2.28 ppm, br m chitosan; 2.50 ppm br m, chitosan; 3.51 br m chitosan overlapping with PEG; 4.55 ppm br m, chitosan). Since no significant amounts of chitosan or free PEG were present in the product, the degree of PEGylation could be calculated from the weight of PEG attached to the chitosan (wt. of PEGylated chitosan—weight of chitosan). The number of moles of amine on the chitosan was calculated using 200 KDa for the chitosan molecular weight, calculating the number of glucosamine corresponding to 200 Kda, and subtracting 0.1 moles of these units due to the presence of approximately 10% acetylation.

EXAMPLE 7

Formation of a hydrogel by pPEGylation of chitosan using $PEG_{3400}$ di(acetaldehyde diethylacetal)

$PEG_{3400}$ di(acetaldehyde diethylacetal) was prepared from $PEG_{3400}$ and chloroacetaldehyde diethylacetal by the method described for $mPEG_{2000}$ in (1) above. In a typical experiment, 100 mg of chitosan was dissolved in 25 ml of 2% HOAc (pH 2.6) and 630 mg of $PEG_{3400}$ di(acetaldehyde diethylacetal) was added. The resulting solution was heated at 75° C. for 20 minutes. After cooling to room temperature, 100 mg of $NaCNBH_3$ was added and the resulting mixture sonicated. A gel formed within 2 minutes. Using HO—PEG—OH and chitosan under the same conditions, no gel formed. Also, no gel formed in the absence of NaCNBH$_3$. The gel was washed repeatedly with distilled water, freeze-dried, and rehydrated and the degree of swelling: [(wt wet—wt dry)/wt dry] was determined to be approximately 33. The product was a soft gel stable at room temperature.

EXAMPLE 8

Pegylation of lysozyme

In a typical preparation, 20 mg of $mPEG_{2000}$ diethylacetal was dissolved in 1 ml of 25 mM phosphoric acid (pH 2.1) and the resulting solution was heated at 50!C. for 1 hour then cooled to room temperature. The pH of the solution was then adjusted to 6 with 0.1M sodium phosphate and the resulting solution added to a solution of 6 mg of in 0.5 ml of 0.1M sodium phosphate buffer (pH 6). After 1 hour, 0.1 ml of 25 mM aqueous $NACNBH_3$ was added. Aliquots (75 ul) were withdrawn at timed intervals from the reaction mixture, diluted with 75 ul of 25 mM phosphoric acid (pH 2.1) and the resulting solution was analyzed by capillary electrophoresis (CE). CE analysis indicated the presence of PEG derivatives of lysozyme having 1, 2, 3, and 4 PEGs attached. Matrix Assisted Laser Desorption Ionization Time-of-Flight (MALDI-TOF) mass spectrometry displayed peaks for four PEGylated derivatives of lysozyme at 16681 Da, 18730 Da, 20760 Da, and 22771 Da, differing in mass by approximately 2000 Da. The mass of unmodified (native) lysozyme by MALDI-TOF was 14,537.

Although the forgoing invention has been described in some detail by way of illustration and example for purpose of clarity of understanding, it will be apparent to a person skilled in the art that certain changes and modifications may be practiced within the scope of the appended claims.

That which is claimed is:

1. A method for conjugating a water soluble polymer to a substance having an amine group, comprising:

providing a polymer precursor by linking to said polymer a moiety having the formula of

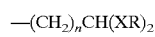

OR

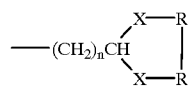

wherein n is a number of from 1 to 6, X is the atom of O or S, and R is an alkyl group;

converting said polymer precursor to an activated polymer having an aldehyde hydrate moiety; and reacting said substance with the polymer having an aldehyde hydrate moiety and forming a linkage between the substance and the water soluble polymer.

2. The method of claim 1 wherein said step of converting said polymer precursor to an activated polymer having an active aldehyde hydrate moiety is conducted in situ with water at an acidic pH.

3. The method of claim 1 wherein said step of reacting said substance with the activated organic polymer comprising adding a reducing reagent.

4. The method of claim 3 wherein said reducing reagent is sodium cyanoborohydride.

5. The method of claim 1 wherein said moiety is acetaldehyde diethyl acetyl.

6. The method of claim 1 wherein said moiety is propionaldehyde diethyl acetyl.

7. The method of claim 1 wherein said polymer is selected from the group consisting of poly(ethylene glycol), poly(vinyl alcohol), poly(alkylene oxides), poly(oxyethylated polyols), poly(olefinic alcohols), poly(acryloyl morpholine), poly(vinyl pyrrolidone), poly(oxazoline), dextran, poly(hydroxyethyl methacrylate), and derivatives thereof.

8. The method of claim 1 wherein said polymer is poly(ethylene glycol).

9. The method of claim 1 wherein said polymer has a formula of Z—O—(CH$_2$CH$_2$O(CH$_2$CH$_2$O)$_m$CH$_2$CH$_2$OH wherein m equals about 5 to 3000, Z is selected from the group consisting of hydrogen, alkyl groups, benzyl groups and aryl groups.

10. The method of claim 1 wherein the polymer is methoxy-poly(ethylene glycol).

11. The method of claim 1 wherein the polymer is a hydrolytically degradable form having a formula of Z—O—CH$_2$CH$_2$O(CH$_2$CH$_2$O)$_m$(CH$_2$)$_r$—CO$_2$—(CH$_2$CH$_2$O)$_s$CH$_2$CH$_2$OH in which m and s may be the same or different and range from about 5 to about 3000, r ranges from 1 to 6, and Z is selected from the group consisting of hydrogen, alkyl groups, benzyl groups and aryl groups.

12. The method of claim 1 wherein said polymer is a polymer having a formula of Q$_y$, wherein Q is a branching core moiety, poly represents a polymer selected from the group consisting of poly(ethylene glycol), poly(vinyl alcohol), poly(alkylene oxides), poly(oxyethylated polyols), poly(olefinic alcohols), poly(acryloyl morpholine), poly(vinyl pyrrolidone), poly(oxazoline), dextran, poly(hydroxyethyl methacrylate), and derivatives thereof, y is an integer of from 2 to 100.

13. The method of claim 12 wherein the Q is a moiety selected from the group consisting of glycerol, lysine, pentaerythritol.

14. The method of claim 1 wherein said activated polymer has a formula of

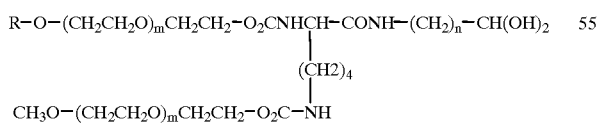

wherein m is from 5 to 3000, and n is from 1 to 6.

15. The method of claim 1 wherein said substance is selected from the group consisting of protein, peptide, oligonucleotides, polysaccharide and drug molecules.

16. A method of making a hydrogel from an amine-containing biomaterial and a water soluble polymer comprising:

providing a polymer precursor by linking to said polymer at least two moieties each having the formula of —(CH$_2$)$_n$CH(XR)$_2$

OR

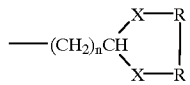

wherein n is a number of from 1 to 6, X is the atom of O or S, and R is an alkyl group;

converting said polymer precursor to an activated organic polymer having at least two active aldehyde hydrate moieties, wherein the linkage between the polymer and each aldehyde hydrate moiety is stable against hydrolysis; and reacting said biomaterial with the activated organic polymer having at least two active aldehyde hydrate moieties and forming a linkage between the substance and the water soluble polymer.

17. The method of claim 16 wherein said step of converting said polymer precursor to an activated organic polymer having an active aldehyde hydrate moiety is conducted in situ with water at an acidic pH.

18. The method of claim 16, wherein said biomaterial is selected from the group consisting of aminopolysaccharides, peptides, and proteins.

19. The method of claim 16, wherein said polymer precursor is has a formula of (CH$_3$CH$_2$O)$_2$CH—(CH$_2$)$_n$—O—(CH$_2$CH$_2$O)$_m$(CH$_2$)$_n$—CH(OC$_2$H$_5$)$_2$ wherein m equals about 5 to 3000, and n is an integer of 1 to 6.

20. A method for preparing an aldehyde derivative of a water soluble polymer comprising:

providing a polymer precursor by linking to said organic polymer a moiety having the formula of —(CH$_2$)$_n$CH(XR)$_2$

OR

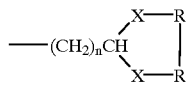

wherein n is a number of from 1 to 6, X is the atom of O or S, and R is an alkyl group;

converting said polymer precursor to an activated organic polymer having an active aldehyde hydrate moiety, wherein the linkage between the polymer and the aldehyde hydrate moiety is stable against hydrolysis;

extracting the activated polymer into an organic solvent; and removing said solvent by distillation in an inert atmosphere whereby the aldehyde derivative of the water soluble organic polymer is obtained.

21. The method of claim 20 wherein said aldehyde derivative has a formula of

RO—(CH$_2$CH$_2$O)$_m$CH$_2$CH$_2$—O—CH$_2$]$_2$CH—O—(CH$_2$)$_n$—CH=O wherein R=H or alkyl or benzyl; m=about 5 to 3000; and n is from 1 to 6.

22. The method of claim 19 wherein said aldehyde derivative has a formula of

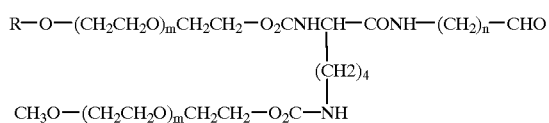

in which m is from about 5 to 3000, and n is from 1 to 6.

23. An aldehyde derivative of a water soluble polymer selected from the group consisting of poly(alkylene oxides), poly(vinyl alcohol), poly(oxyethylated polyols), poly(olefinic alcohols), poly(acryloyl morpholine), poly(vinyl pyrrolidone), poly(oxazoline), poly(hydoxyethyl methacrylate, dextran and derivatives thereof, comprising a functional moiety linked to said water soluble polymer, said moiety having the formula of

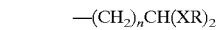

OR

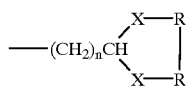

wherein n is a number of from 1 to 6, X is the atom of O or S, and R is an alkyl group.

UNITED STATES PATENT AND TRADEMARK OFFICE
CERTIFICATE OF CORRECTION

PATENT NO. : 5,990,237
DATED : November 23, 1999
INVENTOR(S) : Bentley et al.

It is certified that error appears in the above-identified patent and that said Letters Patent is hereby corrected as shown below:

Title page, insert the following:

--Related U.S. Application Data

Provisional Application No. 60/047,327, May 21, 1997--.

In the References Cited, OTHER PUBLICATIONS, line 2, before "Conjugates" insert --Relevant--; lines 4 and 5, "Monomethoxpoly" should read --Monomethoxypoly--.

Col. 9, line 55, "50!C." should read --50°C.--.

Col. 10, line 10, "50!C." should read --50°C.--; line 18, in the third sub-heading "Temperature (?C)" should read --Temperature (°C.)--; line 31, "40-50!C." should read --40-50°C.--; line 32, "50!C." should read --50°C.--.

Col. 11, line 40, "65!C." should read --65°C.--.

Col. 12, line 27, "50!C." should read --50°C.--.

Col. 13, lines 9-10, "comprising" should read --comprises--; line 41, "$Q_y$" should read --$Q[poly]_y$--; line 57, in the formula, "(CH2) $_4$" should read --$(CH_2)_4$--.

UNITED STATES PATENT AND TRADEMARK OFFICE
CERTIFICATE OF CORRECTION

PATENT NO. : 5,990,237
DATED : November 23, 1999
INVENTOR(S) : Bentley et al.

It is certified that error appears in the above-identified patent and that said Letters Patent is hereby corrected as shown below:

Col. 14, line 31, after "precursor" cancel "is"; line 62, in the formula, at the beginning "RO" should read --[RO--; line 66, "said" should read --the--.

Col. 15, line 3, in the formula, "(CH2) $_4$" should read --$(CH_2)_4$--; lines 13-14, "poly(hydoxyethyl methacrylate" should read --poly(hydroxyethyl methacrylate)--.

Signed and Sealed this

Twenty-second Day of August, 2000

Attest:

Q. TODD DICKINSON

*Attesting Officer*   *Director of Patents and Trademarks*